United States Patent [19]

Jutsum

[11] Patent Number: 4,743,592

[45] Date of Patent: May 10, 1988

[54] METHOD OF COMBATING SOIL PESTS OF PLANTS BY EMPLOYING ACTIVE MACROLIDE SUBSTANCES INJECTED INTO SAID PLANTS

[75] Inventor: Alan R. Jutsum, Berkshire, England

[73] Assignee: Imperial Chemical Industries PLC, London, England

[21] Appl. No.: 890,887

[22] Filed: Jul. 28, 1986

Related U.S. Application Data

[63] Continuation of Ser. No. 681,623, Dec. 14, 1984, abandoned.

[30] Foreign Application Priority Data

Jan. 18, 1984 [GB] United Kingdom ............... 8401280

[51] Int. Cl.$^4$ ...................... A01N 43/02; A01N 43/04
[52] U.S. Cl. ......................................... 514/30; 514/450
[58] Field of Search ................................... 514/30, 450

[56] References Cited

FOREIGN PATENT DOCUMENTS 0076580 4/1983 European Pat. Off. .

OTHER PUBLICATIONS

Putter et al., (Experientia, vol. 37, (1981), pp. 963–964.
Sasser et al., (Plant Disease, vol. 66(8), (1982), pp. 691–693.
Keil; Agricultural Chemical; pp. 23, 24 and 28, Apr. 1965.

*Primary Examiner*—Allen J. Robinson
*Attorney, Agent, or Firm*—Cushman, Darby & Cushman

[57] ABSTRACT

Soil dwelling nematode pests of growing plants are combated and controlled by injecting or infiltrating into the stem of the plants an effective amount of an insecticidally active macrolide substance, such as, for example, an avermectin or milbemycin.

3 Claims, No Drawings

METHOD OF COMBATING SOIL PESTS OF PLANTS BY EMPLOYING ACTIVE MACROLIDE SUBSTANCES INJECTED INTO SAID PLANTS

This is a continuation of application Ser. No. 681,623, filed Dec. 14, 1984, now abandoned.

This invention relates to a method of combating nematode pests of plants and to compositions for use in the method.

Nematodes are economically important pests of agriculture which affect adversely the yields of many food and fibre crops. The nematodes are soil dwelling pests which attack the roots of plants. They are difficult to control and measures proposed previously involve fumigation of the soil with volatile halocarbon toxicants such as dichlorodibromopropene or treatment of the soil with nematocidally active insecticides such as oxamyl or carbofuran. It has long been recognised that the most effective treatment would be one in which the toxicant is applied to the aerial parts of the plant by spraying or dusting and is then translocated to the roots to combat and control the nematode pests surrounding and attacking the roots by this method has never been very successfully practiced with the known toxicants because they do not have adequate translocation properties.

We now discovered that certain macrolide antibiotic materials have both the necessary translocation and the nematocidal properties to permit the successful and practical application of this desirable method of nematode control.

In our European patent application No. 82304813.7 we describe a method of combating and controlling soil dwelling nematode pests of growing plants rooted in the soil and susceptible to damage by nematode pests which comprises applying to the aerially exposed parts of the plant, a nematocidally effective amount of an insecticidally active macrolide substance, preferably one selected from the groups consisting of C-076 and B-41 antibiotics and their simple derivatives (including acylated derivatives, aglycones, and the like).

Although this method works well for a wide variety of plants there are clearly some disadvantages when the plants are large, eg. citrus trees, since overspraying the foliage is not always an easy operation and the quantity of active material actually reaching the roots by translocation is a relatively small proportion of that which is actually applied, which affects the economics of the operation.

We have now discovered that these disadvantages can be overcome by the use of an injection or infiltration technique whereby the C-076 or B-41 antibiotic substance can be fed into the stem of the plant at a position intermediate the soil level and the foliage.

Accordingly the present invention provides an improved method for the control of soil dwelling nematode pests of growing plants rooted in the soil and susceptible to damage by nematode pests which comprises injecting or infiltrating into the stem of the plant at a position intermediate the soil level and the aerial foliage of the plant a nematocidally effective amount of an insecticidally active macrolide substance selected from the group consisting of C-076 and B-41 antibiotics and their simple derivatives.

C-076 and B-41 macrocyclic antibiotic substances and their derivatives (hereinafter called the active ingredients) are fully described in the following patents (the disclosures of which are herein incorporated by reference) viz. U.S. Pat. Nos. 3998699, 3992527, 3992551, 3992552, 3984564, 3950360, 4134973, 4093629, 4199569, 4206205, 4201861, 4171314 and 4203976, British Patent Nos. 1573955 and 1390336 and published Netherlands Patent Application No. 8004791A and European Patent Application No. 0008184. Such C-076 antibiotics are also known as avermectins and B-41 antibiotics are also known as milbemycins. Particular examples of C-076 antibiotics useful in the invention method include that known as avermectin $B_{1a}$ the structure of which is given by Chabala et al, J. Agric Food Chem 1981, 29, 881–884 at 885, and that known as Ivermectin which is the 22,23-dihydro derivative of avermectin $B_{1a}$ and has the structure:

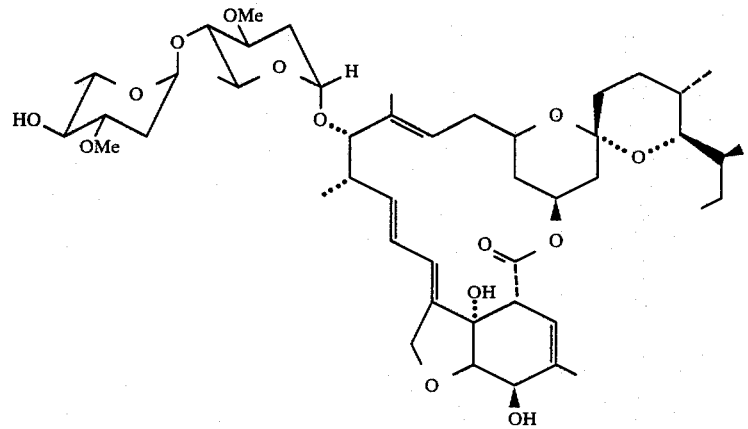

A particular example of a B-41 macrolide substance is that known as milbemycin B-41D which is described in Netherlands Patent Application No. 8004791A, having the structure:

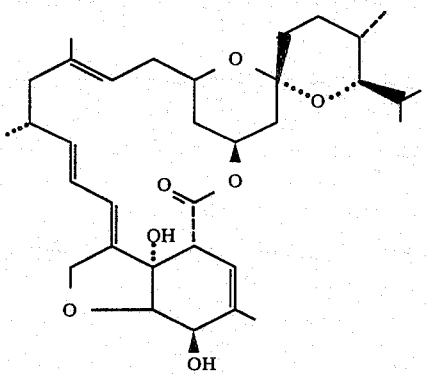

C-076 and B-41 macrolide substances are obtained by fermentation process using certain Streptomyces species.

A particularly useful C-076 producing Streptomyces species is that known as *Streptomyces avermitilis* a culture of which has been deposited in the permanent culture collection of the Fermentation Section of the Northern Utilization Research Branch, U.S. Department of Agriculture at Peoria, Ill., USA and has been assigned the accession number NRRL 8165. A further sample of this culture has been deposited, without restriction as to availability, in the permanent culture collection of the American Type Culture Collection at 12301 Parklawn Drive, Rockville, Md. 20852, USA, and has been assigned the accession number ATCC 31267. Other strains and mutants of *S. avermitilis* may also be used in this invention process, including, for example, those deposited at the American Type Culture Collection under the accession numbers ATCC 31271 and 31272.

A particularly useful B-41 producing Streptomyces species is that known as the B41-146 strain (fully described in U.S. Pat. No. 3,984,564) which has been deposited at the Research Institute of Industrial Technology of Micro-organisms, Agency of Industrial Science and Technology of Japan, under the deposition number Bikokenkinki no 1438, and at Northern Research Laboratory, U.S. Department of Agriculture, Peoria, Ill., USA under the deposit number NRRL 5739. The process of producing B-41D is set forth in U.S. Pat. No. 4,346,171 the disclosure of which is herein incorporated by reference.

A yet further macrolide substance produced by a Streptomyces species which may also be useful in the method of the invention is that described in published European Patent Application no. 0050964 (the disclosure of which is herein incorporated by reference), a sample of which has been deposited at the American Type Culture Collection under the accession number 31587.

The method of the invention is preferably performed by directly injecting into the stem of the plant a liquid composition, for example using a compressed air activated injection system, or alternatively infiltrating a liquid composition into the stem through for example a hollow cannula using gravity feed over a elapsed time period. A capillary feeding device may be used instead of a cannula, or alternatively a controlled release pellet may be injected into the stem. The compositions suitable for use in this method may contain from 0.00001% to 1% by weight of the active ingredient.

The method is particularly suitable for use on crops having aerial foliage widely separated from the soil level by a stem, especially a woody stem, such as citrus or bananas.

Species of nematodes which may be controlled by the invention method include the following:

| | |
|---|---|
| *Globodera rostochiensis* | (potato cyst nematode) |
| *Heterodera schachtii* | (beet cyst nematode) |
| *Meloidogyne incognita* | (root knot nematode) |
| *Meloidogyne javanica* | (tobacco root knot nematode) |
| *Pratylenchus penetrans* | (lesion nematode) |
| *Radopholus similis* | (burrowing nematode) |
| *Tylenchulus semipenetrans* | (citrus nematode) |

The translocation of the active ingredient from the stem to the roots, which is believed to be via the phloem system of the plant, is extremely rapid and nematode damage the soil to the roots is prevented or significantly reduced. The treatment provides both rapid and long lasting control. Thus nematodes are controlled to an extent of 90% or more for a period of more than two weeks after injecting an ivermectin composition containing 0.1% by weight of the active ingredient. The treatment causes the root to produce a nematode controlling exudate which probably contains the macrolide or a derivative or metabolite thereof. This exudate can be collected for at least two weeks after treatment by washing the roots of the treated plants and can be shown to be active against nematodes of the species *Meloidogyne incognita*.

Compositions for use in the invention include liquid compositions obtained by water dilution of emulsifiable concentrates, suspension concentrates, soluble liquid compositions and the like. Such compositions may contain from 0.00001 to 1.0% by weight of the macrolide substance. The concentrated compositions, in the form in which they are prepared, transported and stored, may contain from 0.5 to 50% by weight of the macrolide, depending upon the type of composition. Generally soluble liquid compositions have lower concentrations of active ingredient than emulsifiable concentrates or suspension concentrates. The compositions also contain surface active agent (emulsifying agents) in an amount from 1 to 20% by weight. These surface agents are usually selected from anionic types such as alkali metal or alkaline earth metal salts of sulphosuccinate or lignosulphonic acids, eg. sodium dioctylsulphosuccinate, sodium and calcium lignosulphonates, and nonionic types such as ethoxylated alkyl phenols and alcohols, eg. ethoxylated nonylphenol. Suspension concentrates may also contain antisettling agents such as bentonite to improve the shelf life of the compositions.

Other compositions which may be useful in performing the invention include pellets containing the active ingredient which can be injected into the stem of the plant (particularly those with woody stems) and from which the active ingredient is slowly released over a prolonged period.

The method of the invention is illustrated by the following Examples.

EXAMPLE 1

A solution of ivermectin (5 ml of a preparation containing 10000 ppm) was infiltrated passively via "Keristicks" into the stems of tomato plants in a replicated test. "Keristicks" (Trade Mark of Imperial Chemical Industries PLC) are solid capillary wicks made from cellulose acetate and are normally used to introduce water from a reservoir into the soil of a plant pot in a controlled manner. 48 hours after treatment the soil supporting each plant was inoculated with ca. 800 larval root knot nematodes (*Meloidogyne incognita*). 21 days after inoculation the degree of nematode control was assessed by counting the number of root knots and recording the phytotoxic effect of the treatments. The results obtained show that infiltration of ivermectin reduced the number of root knots by a value of 91% compared with the control without any phytotoxic effect. When the known nematicide oxamyl was applied in similar manner at the same rate (expressed as weight/plant: actually 4.13×molar rate) 81% reduction was observed but the application also caused foliar phytotoxicity (scored leaf tips).

EXAMPLE 2

The improvement in delivery of the antibiotic to the roots by the method of the invention was determined by infiltrating tritiated ivermectin into the stems of water-stressed tomato seedlings and radiochemical distribution between the root and root tissue exudate determined at time intervals up to 14 days after treatment. The results are given in the following table as a percentage of the amount of chemical applied.

|  | % tritiated material recovered after | | | |
| --- | --- | --- | --- | --- |
|  | 1 day | 3 days | 7 days | 14 days |
| Root exudate | 1.2 | 1.3 | 23.6 | 21.2 |
| Root tissue | 0.8 | 2.0 | 11.6 | 9.6 |

This compares with <0.2% of material applied to the foliage being recovered from root exudate after 14 days.

EXAMPLE 3

This Example illustrates an emulsion concentrate suitable for application, when diluted, in the method of the invention.

| Ingredient | % w/w |
| --- | --- |
| Ivermectin | 10.0 |
| 'Aerosol' OT | 3.0 |
| 'Synperonic' OP10 | 7.0 |
| 'Solvesso' 100 to | 100 |

('Aerosol', 'Synperonic' and 'Solvesso' are Registered Trade Marks)

'Aerosol' OT is an anionic emulsifying agent based on sodium dioctylsulphosuccinate. 'Synperonic' OP10 is a nonionic emulsifying agent based on ethoxylated octylphenol. 'Solvesso' 100 is a solvent blend of lower alkylated benzenes).

EXAMPLE 4

This Example illustrates a soluble liquid composition suitable for use in the method of the invention.

| Ingredient | % w/w |
| --- | --- |
| Ivermectin | 1.0 |
| 'Synperonic' A20 | 10.0 |
| Diacetone alcohol to | 100 |

('Synperonic' A20 is a nonionic emulsifying agent based on ethoxylated alcohol).

EXAMPLE 5

This Example illustrates a suspension concentrate suitable after dilution with water for use in the method of the invention.

| Ingredient | % w/w |
| --- | --- |
| Ivermectin | 10.0 |
| 'Polyfon' H | 2.0 |
| 'Synperonic' NX | 1.0 |
| Bentonite | 2.0 |
| Water to | 100 |

('Polyfon' is a Registered Trade Mark. 'Polyfon' H is an anionic emulsifying agent based on sodium lignosulphonate. 'Synperonic' NX is a nonionic emulsifying agent based on ethoxylated nonyl phenol).

The preceding Examples of compositions for use in the method of the invention illustrate ivermectin as the macrolide ingredient. Similar compositions may be prepared using other macrolide substances such as avermectin $B_{1a}$, milbemycin B-41D, and the like in place of ivermectin.

What is claimed is:

1. In a process for the cultivation of a living plant rooted in plant parasitic nematode infested soil which comprises treating the plant with a nematicidal composition having as active ingredient a nematicidally effective amount of a macrolide substance selected from the group consisting of C-076 and B-41 antibiotic substances in association with an aqueous liquid diluent which may also comprise a surface active agent, the improvement which comprises injecting or infiltrating the said composition into the stem of the plant at a position intermediate to the soil level and the aerial foliage of the plant, whereby a nematicidally effective amount of the macrolide substance is translocated downwardly to the roots of the plant and nematode damage is thereby controlled.

2. The process of claim 1 wherein the macrolide substance is avermectin $B_{1a}$.

3. The process of claim 1 wherein the nematicidal composition is infiltrated into the stem of the plant via a capillary feeding device comprising a solid capillary wick.

* * * * *